United States Patent [19]

Loeb et al.

[11] Patent Number: 4,888,007
[45] Date of Patent: Dec. 19, 1989

[54] PUBIC PROPHYLACTIC

[75] Inventors: Marvin P. Loeb, Huntington Beach, Calif.; John F. Perry, Vernon Hills, Ill.

[73] Assignee: Xtramedics, Inc., Deerfield, Ill.

[21] Appl. No.: 81,353

[22] Filed: Aug. 4, 1987

[51] Int. Cl.⁴ ............................................. A61F 5/42
[52] U.S. Cl. ..................................... 604/352; 128/844
[58] Field of Search ................... 128/132 R, 830, 842, 128/844; 604/349, 346, 350, 351, 352, 353, 355, 317, 327, 332, 337, 338, 339, 342–345

[56] References Cited

U.S. PATENT DOCUMENTS

| | | | |
|---|---|---|---|
| 1,687,717 | 10/1928 | Epstein | 604/349 |
| 1,711,294 | 4/1929 | Weitzner | 128/361 |
| 2,305,453 | 12/1942 | Martos | 128/132 R |
| 2,591,783 | 4/1952 | Craddock | 604/353 |
| 3,136,417 | 6/1964 | Clinch | 604/349 |
| 3,401,697 | 9/1968 | Lefley et al. | 604/352 |
| 3,677,225 | 7/1972 | Czirely | 604/352 |
| 3,739,783 | 6/1973 | Broerman | 604/352 |
| 4,359,051 | 11/1982 | Oczkowski | 604/344 |
| 4,640,688 | 2/1987 | Hauser | 604/352 |
| 4,794,920 | 1/1989 | Robichaud | 128/844 |

FOREIGN PATENT DOCUMENTS

| | | | |
|---|---|---|---|
| 1158507 | 12/1983 | Canada | 604/349 |
| 1595711 | 8/1981 | United Kingdom | 604/349 |
| 8605681 | 12/1986 | World Int. Prop. O. | 604/349 |

Primary Examiner—C. Fred Rosenbaum

[57] ABSTRACT

A pubic shield securable to the user is disclosed. The shield may or may not have a condom unitary therewith. Securement is achieved by means of a bioadhesive, which may contain biocide or the like ingredient.

12 Claims, 3 Drawing Sheets

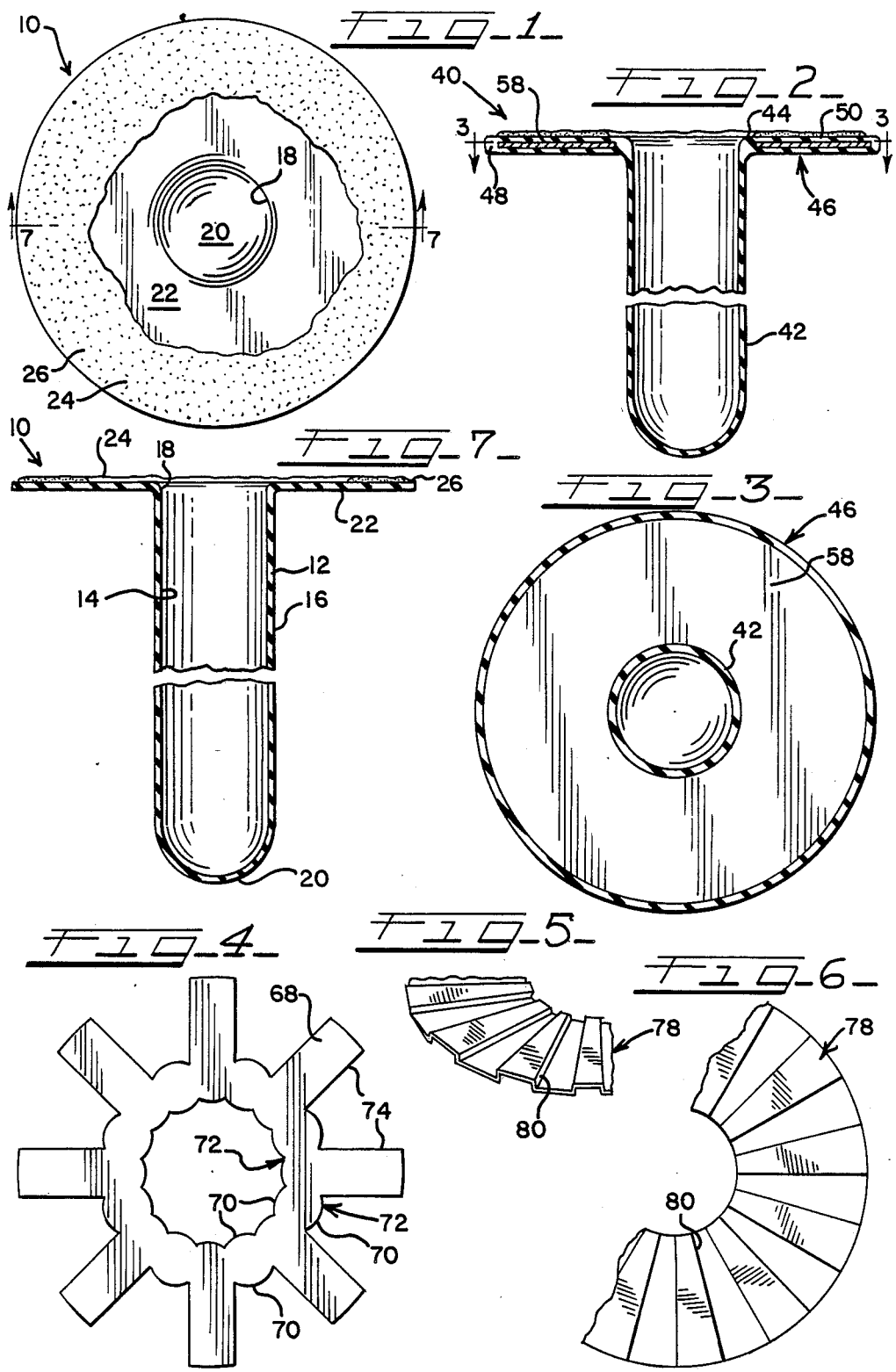

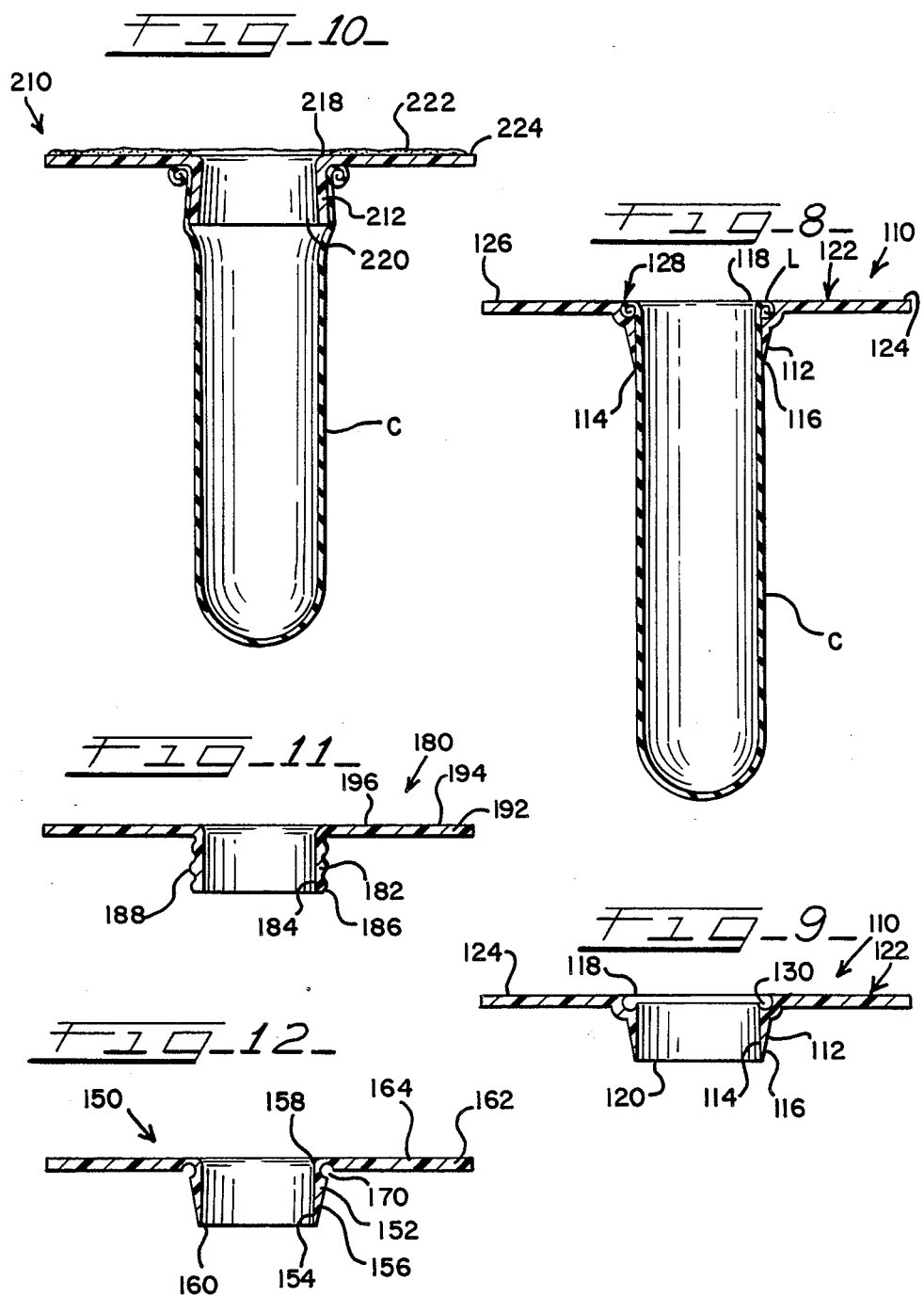

PUBIC PROPHYLACTIC

FIELD OF THE INVENTION

The present invention pertains to hygienic appliances, and more particularly to a pubic shield as a male contraceptive and prophylactic device.

BACKGROUND OF THE INVENTION

The incidence of venereal disease is increasing, and the number of people infected each year with all types of venereal disease is rising at an alarming rate. A recently diagnosed, and most deadly, sexually transmitted disease is acquired immune deficiency syndrome (AIDS). With respect to AIDS, there has been a growing awareness of the potential for transmitting the virus responsible for inducing AIDS through minor skin abrasions. In addition, it has been shown that this virus is present in vaginal fluids. While the use of a conventional condom decreases the likelihood of contracting AIDS or other sexually transmitted diseases, it would be desirable to have a more effective prophylactic.

Because of the role the condom plays in prevention of venereal disease, there has become a heightened interest in the configuration of the condom itself. While prior developments had centered on durability and material variations, see, for example U.S. Pat. Nos. 4,406,853 to Miyata and 4,527,988 to Lutz et al., the configuration of the condom itself is now undergoing scrutiny.

Problems associated with the use of condoms include: slippage, allowing some body fluids to leak in or out; tearing while donning or removing; and insufficient protection of the pubic region from exposure to body fluids that may contain an AIDS-inducing virus.

The present invention contemplates a device that provides enhanced prophylactic benefit for external, male-worn, contraceptive devices, is comfortable to wear, and easy to don and remove.

SUMMARY OF THE INVENTION

The present invention provides a pubic shield which has a shield portion and, optionally, a unitary condom portion in association therewith. The shield portion is securable to the user by means of a bioadhesive. The condom portion comprises an elastic tubular sheet having an open proximal end and a closed distal end. An outwardly extending pubic shield member is located about the periphery of the tubular sheet at the proximal end thereof and the bioadhesive is provided on at least a portion of a contact face defined by the outwardly extending shield member. This construction provides improved protection for the wearer by increasing the shielded area without a sacrifice in comfort.

In one embodiment of this invention, the condom and the outwardly extending shield member are unitary. The shield member is substantially a stiffened continuation of the relatively thin tubular sheet material forming the prophylactic sheath of the condom. The outwardly extending shield member is stiff enough to be substantially self-supporting but flexible enough to conform to the human body.

The pubic shield, however, can also be separate from but configured to receive a conventional condom. To that end the pubic shield can include a resilient tubular element open at both the proximal end and the distal end in association with an integral, outwardly-extending shield member located about the periphery of the tubular element. An attachment means for securing a conventional condom to the tubular portion is provided and may include an adhesive. A bioadhesive is present on the outwardly extending shield member for securement to the pubic region of the user. Such a pubic shield can be disposable or reusable. The bioadhesive can contain a biocide. In addition, the pubic shield of this invention can be packaged in a sealed package with a lubricant, biocide, and the like.

A disposable version of the present pubic shield may have absorbent properties vis-a-vis body fluids as well.

Numerous other advantages and features of the invention will become readily apparent from the following detailed descriptions of the invention, the accompanying drawings, and the claims.

BRIEF DESCRIPTION OF THE DRAWINGS

The accompanying drawings form part of the specification. In these drawings, like numerals are used to designate like parts throughout the same and FIG. 1 is a top plan view of a pubic shield embodying the present invention;

FIG. 2 is a cross-sectional elevational view of an alternative embodiment of the pubic shield;

FIG. 3 is cross-sectional elevational view taken along plane 3—3 of FIG. 2;

FIG. 4 is a plan view showing an alternative preferred embodiment of a shield stiffener suitable for use in the present invention;

FIG. 5 is an enlarged, fragmentary perspective view of another preferred embodiment of a shield stiffener for the present invention;

FIG. 6 is a fragmentary plan elevational view of yet another preferred embodiment of a shield stiffener for the present invention;

FIG. 7 is a cross-sectional elevational view taken along plane 7—7 of FIG. 1;

FIG. 8 is a cross-sectional elevational view of a pubic shield embodying the present invention and shown with a conventional condom in place;

FIG. 9 is a cross-sectional elevational view of the pubic shield shown in FIG. 8;

FIG. 10 is a cross-sectional elevational view of an alternative embodiment of the present pubic shield and shown with a condom attached;

FIG. 11 is a cross-sectional elevational view of a further embodiment of a pubic shield of the present invention;

FIG. 12 is a cross-sectional elevational view of a still further embodiment of a pubic shield of the present invention;

DESCRIPTION OF THE PREFERRED EMBODIMENT

Figure 13:
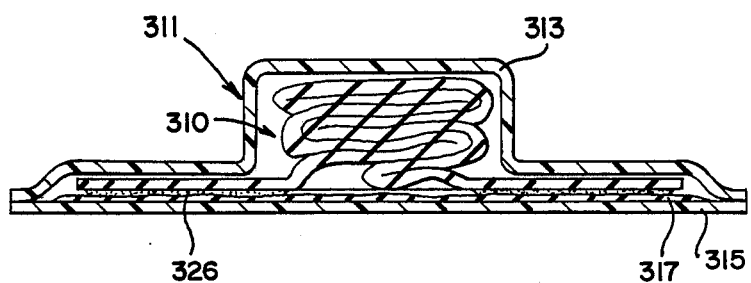
FIG. 13 is an enlarged cross-sectional elevational view showing a packaged pubic shield with a unitary condom.

The invention disclosed herein is, of course, susceptible of embodiment in many different forms. Shown in the drawing and described hereinbelow in detail are certain preferred embodiments of the present invention. It is to be understood, however, that the present disclosure is an exemplification of the principles of this invention and does not limit the invention to the illustrated embodiments.

FIGS. 1 through 7 illustrate a pubic shield that includes a condom unitary therewith and alternative features. FIGS. 9 through 12 illustrate a pubic shield and its alternative features for use with a conventional condom.

Referring to FIGS. 1 and 7, pubic shield 10 includes an elastic, tubular sheet 12 having an inner surface 14, an outer surface 16, open proximal end 18, and a closed distal end 20. The pubic shield 10 further includes an outwardly extending shield member 22 about the periphery of the tubular sheet 12 at the proximal end 18 thereof. The shield member 22 defines a contact face 24 that is continuous with the inner surface 14 of the tubular sheet 12, and a bioadhesive 26 on the contact face 24. Portions of shield member 22 may be absorbent with respect to body fluids.

The elastic tubular sheet 12 and the outwardly extending shield member 22 can be either unitary with one another or integral with one another.

Size of the shield member can vary as desired. Preferably the shield member has an outer diameter of about 5 to about 7 inches.

The outwardly extending shield member 22 of the pubic shield 10 includes a shield stiffener. In the embodiment illustrated in FIGS. 1 and 7, the stiffener is the bioadhesive 26 itself. FIGS. 2 through 6 illustrate various additional embodiments of other shield stiffeners.

Pubic shield 40 of FIG. 2 is similar in construction and mode of operation to pubic shield 10. The difference between shield 10 and shield 40 is the type of shield stiffener that is utilized. The shield 40 includes elastic tubular sheet 42, shield member 46 having a contact face 44, and a shield stiffener 58 that is embedded within shield member 46. Shield 40 also includes a bioadhesive 50 on its contact face 44. The shield stiffener may also be bonded to the shield on one or both surfaces thereof.

The shield stiffener embeded within the shield member 46 can have various configurations. Alternatives to the disc-type stiffener 58 shown in FIG. 3 are the scallop stiffener 68 shown in FIG. 4, the fluted stiffener 78 shown in FIG. 6, and the like. These shield stiffeners will be discussed individually in detail hereinbelow.

When the shield stiffener is embedded within the shield or flange material, no contact with human skin is possible, so the shield stiffener can be made of a wide variety of materials. For example, FIG. 3 shows a disc shaped stiffener 58. The disc can be made out of paper, cardboard, woven or non-woven fabric, flexible plastic, or other convenient material that imparts stiffness to the flange assembly. As the bioadhesive 50 is also applied to the contact face 44, the contribution to stiffness of the stiffener 48 must be considered in combination with the additional stiffness contributed by the bioadhesive 50.

Alternatively, the shield stiffener can be made of a relatively absorbent material, and perforations can be provided in the shield stiffener to provide channels of communication to the encapsulated, relatively absorbent material so that body fluids of the wearer's sexual partner can be absorbed and retained within the shield stiffener.

FIG. 4 shows a scallop stiffener 68 which includes a scalloped ring 72 and radially outwardly extending spokes 74. In a manner similar to the disc stiffener 58 shown in FIG. 3, the scallop stiffener 68 is embeded in the shield member 46. The scallops 70 on the inner and outer periphery of the scalloped ring 72 also serve as stress relief means which provide additional flexibility and add to the ability of the prophylactic device to conform to the human body without damaging the shield member 46. The spokes 74 maintain defined stiffness throughout the surface of the shield member 46.

FIGS. 5 and 6 illustrate yet another stiffener, a fluted stiffener. The generally disc-shaped fluted stiffener 78 includes pleats 80 as stress relief means. As the disc extends across the radius of the shield member 46, proper stiffness is maintained, yet the shield member 46 can conform to a variety of surface contours by stretching or compressing the pleats 80.

FIGS. 8 through 12 show pubic shields embodying the present invention and intended for use with a conventional condom. The pubic shield 110 shown in FIGS. 8 and 9 includes a resilient tubular element 112 open at both ends, having an inner surface 114, an outer surface 116, a proximal end 118 and a distal end 120. The tubular element terminates in an outwardly extending flexible shield member 122 at the proximal end 118. The shield member 122 defines a contact face 124 which is continuous with the inner surface 114 of the tubular sheet 112. A bioadhesive 126 is provided on the contact face 124.

The pubic shield 110 further includes an attachment means 128 on the tubular element for securement of the condom C thereto. The attachment means shown in FIG. 8 and FIG. 9 is of a snap-in type and is defined by a peripheral groove 130 provided on the inner surface 114 of the tubular element 112. The groove 130 as shown in FIG. 9 is dimensioned to receive therewithin a resilient peripheral lip L unitary with the condom C.

Another attachment means is shown in FIG. 10. FIG. 10 illustrates pubic shield 210 with a tubular element 212, a proximal end 218, a distal end 220 and a contact face 224 on flexible flange 222. The tubular element 212 is flared outwardly toward its distal end so that the diameter of proximal end 218 is smaller than the diameter of distal end 220. When the condom C is drawn over the resilient tubular element 212, the built-in taper assists in keeping the condom C in position.

Yet another attachment means is shown in FIG. 11. The pubic shield 180 includes a tubular element 182 with an inner surface 184 and an outer surface 186. The outer surface 186 has a ribbed configuration 188 which interacts with a conventional condom C and provides a condom securement region for the pubic shield. If desired, an adhesive may be provided an outer surface 186 for retaining the condom on the tubular element 182.

Shield member 192 extends outwardly from tubular element 182 and defines a contact surface 194. A bioadhesive 196 is applied to the contact surface 194. The bioadhesive can include a biocide such as a germicide, spermicide, an anti-viral agent, or the like. Bacteriostatic agents can also be utilized if desired.

Similarly, the pubic shield 150 shown in FIG. 12 includes a resilient tubular element 152 open at both ends, having an inner surface 154, an outer surface 156, a proximal end 158, a distal end 160, outwardly extending flexible flange 162, contact face 164 and a groove 170 to act as condom attachment enhancing means. The groove 170 is dimensioned to receive a resilient peripheral lip L unitary with the condom C. The tubular element 152 in FIG. 12 is shown with a taper for additional flexibility at its distal end.

Latex is the preferred material for condoms that are to be used with the pubic shields of this invention. However, other elastomeric materials, including those types of elastomers which contain a spermicide or germicide, can be utilized as well. Materials of construction derived from natural sources such as those described in U.S. Ser. No. 4,406,853 to Miyata can also be used as well for the tubular portion of the pubic shield.

The present shields for protecting the pubic region can also be made of latex or of other elastomeric material such as that illustrated in U.S. Pat. No. 4,589,880 to Dunn et al.

The shield members 22 and 46 on pubic shields 10 and 40, respectively, provide a convenient region for grasping the appliance when donning or removing. Compared to a conventional condom, improved control is gained, resulting in a lower chance of tearing, leaking or spilling.

The present pubic shields have a bioadhesive applied to all or a portion of the contact face. However, a bioadhesive can also be applied to the outer surface, such as outer surface 116 shown in FIGS. 8 and 9, of the tubular element, for enhanced retention of a condom thereon.

A number of bioadhesives are available for use when practicing the present invention. Such bioadhesives are chemical compounds that adhere to human skin or mucus membrane and have long been used to attach buccal compositions or dentures to the mucus membranes of the gums. Bioadhesives are available in many forms, the preferred form being a gel type. An illustrative example is sodium carboxymethylcellulose (NaCMC) dispersed in a polyethylene/mineral oil gel base. Suitable other bioadhesives are described in Gurny et al., Biomaterials 5:336–340 (November, 1984); Ch'ng et al., J. Pharm. Sci 74 (4): 399–405 (April 1985); and Hui et al., Int. J. Pharmaceutics 26:203–213 (1985).

The bioadhesives can include a biocide, thereby increasing further the protection provided by the present pubic shields. Illustrative biocides are germicides, spermicides, certain antibiotics, anti-viral agents, and the like.

FIG. 13 shows a package containing a pubic shield that includes a condom unitary therewith. In particular, pubic shield 310 is contained within a blister package 311 which, in turn, comprises a contoured thermoplastic covering member 313 removably secured to base 315. A silicone release coating 317 is provided on base 315 and pubic shield 310 is adhesively secured thereto by means of bioadhesive 326. Pubic shield 310 can be packaged dry. Alternatively, a lubricant, such as a medical grade silicone lubricant, may be included on the condom portion of the shield as well as a spermicide, a germicide, or the like.

Figure 14:
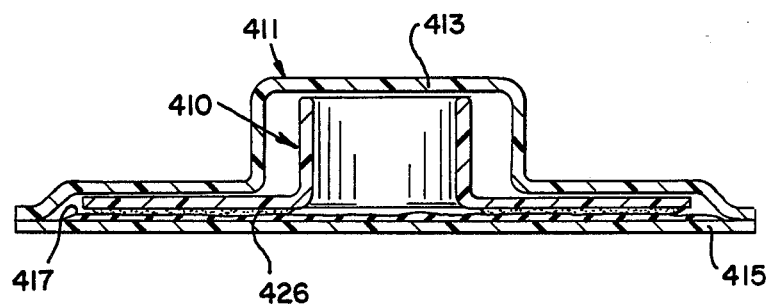
FIG. 14 is an enlarged cross-sectional elevational view showing a packaged pubic shield without a condom.

FIG. 14 illustrates a separate pubic shield 410 packaged in a manner similar to that shown in FIG. 13. In package 411, pubic shield 410 is adhesively secured by means of bioadhesive 426 to package base 415 provided with a silicone release coating 417. Covering member 413 is also secured to base 415 to enclose pubic shield 410.

The foregoing detailed description of the invention and the described embodiments thereof are illustrative. Numerous variations and modifications thereof may be effected without departing from the true spirit and scope of the concepts or principles of this invention. For example, the shield member may be made of a wide variety of materials, including absorbent, spongy materials that absorb body fluids. In the latter instance, all or portion of the shield member can be advantageously formed using a hydrophilic polyurethane or a similar hydrophilic material.

We claim:

1. A condom having a pubic area shield comprising:
   an elastic, tubular sheath member having an inner surface, an outer surface, an open proximal end, and a closed distal end, said sheath member being sized to fit over an erect male organ so as to prevent transmission of fluid between users of said condom;
   an outwardly extending shield member integrally associated with said tubular sheath member about said proximal end thereof, said shield member defining a contact face that is continuous with said inner surface, said shield member being substantially self supporting but flexible enough to conform to the human body in the pubic area; and
   a bioadhesive on said contact face.

2. The condom of claim 1 wherein said elastic tubular sheet and said outwardly extending shield member are unitary with one another.

3. The condom of claim 1 wherein said outwardly extending shield member includes a shield stiffener means.

4. The condom of claim 3 wherein said shield stiffener means includes a stress relief means.

5. The condom of claim 1 wherein said bioadhesive includes a biocide.

6. The shield in accordance with claim 1 contained in a sealed package.

7. A condom having a pubic area shield comprising:
   an elastic, tubular sheath member having an inner surface, an outer surface, an open proximal end, and a closed distal end;
   an outwardly extending shield member integrally associated with said tubular sheath member about said proximal end thereof, said shield member defining a contact face that is continuous with said inner surface, said shield member being substantially self supporting but flexible enough to conform to the human body in the pubic area; and
   a bioadhesive on said contact face; said bioadhesive including a biocide which is an antibiotic.

8. A condom having a pubic area shield comprising:
   an elastic, tubular sheath member having an inner surface, an outer surface, an open proximal end,
   an outwardly extending shield member integrally associated with said tubular sheath member about said proximal end thereof, said shield member defining a contact face that is continuous with said inner surface, said shield member being substantially self supporting but flexible enough to conform to the human body in the pubic area; and
   a bioadhesive on said contact face; said bioadhesive including a spermicide.

9. A pubic area shield for use with a tubular sheath member comprising:
   a resilient tubular element open at both ends, having an inner surface, an outer surface, a proximal end, and a distal end, a radially outwardly extending flattened flexible shield member integrally associated with said tubular element at said proximal end, said shield member defining a contact face continuous with said inner surface, said shield member being substantially self supporting but flexible enough to conform to the human body in the pubic area;
   a bioadhesive on said contact face; and
   attachment means integrally defined on said tubular element for securement of the open end of an elastic, tubular sheath member having a closed opposite end, said attachment means being defined by a groove provided on said inner surface of said tubular element, said groove being dimensioned to receive therewithin a resilient peripheral lip unitary with said sheath member.

10. A public area shield for use with a tubular sheath member comprising:
   a resilient tubular element open at both ends, having an inner surface, an outer surface, a proximal end, and a distal end, a radially outwardly extending flattened flexible shield member integrally associated with said tubular element at said proximal end, said shield member defining a contact face continuous with said inner surface, and said shield member being substantially self supporting but flexible enough to conform to the human body in the pubic area;
   a bioadhesive on said contact face; and
   attachment means integrally defined on said tubular element for securement of the open end of an elastic tubular sheath member having a closed opposite end;
   said bioadhesive including a biocide which is an antibiotic.

11. A pubic area shield for use with a tubular sheath member comprising:
   a resilient tubular element open at both ends, having an inner surface, an outer surface, a proximal end, and a distal end, a radially outwardly extending flattened flexible shield member integrally associated with said tubular element at said proximal end, said shield member defining a contact face continuous with said inner surface, and said shield member being substantially self supporting but flexible enough to conform to the human body in the pubic area;
   a bioadhesive on said contact face; and
   attachment means integrally defined on said tubular element for securement of the open end of an elastic tubular sheath member having a closed opposite end;
   said bioadhesive including a spermicide.

12. A public area shield for use with a tubular sheath member comprising:
   a resilient tubular element open at both ends, having an inner surface, an outer surface, a proximal end, and a distal end, a radially outwardly extending flattened flexible shield member integrally associated with said tubular element at said proximal end, said shield member defining a contact face continuous with said inner surface, and said shield member being substantially self supporting but flexible enough to conform to the human body in the pubic area;
   a bioadhesive on said contact face;
   attachment means integrally defined as a ribbed contour on the outer surface of said tubular element for securement of the open end of an elastic tubular sheath member having a closed opposite end; and
   a bioadhesive provided on said ribber contour.

* * * * *